United States Patent [19]

Offermanns et al.

[11] 3,931,208
[45] Jan. 6, 1976

[54] PROCESS FOR THE PRODUCTION OF THIAZOLINES-(3)

[75] Inventors: Heribert Offermanns, Grossauheim; Friedrich Asinger, Rott; Wolf-Dieter Pfeifer, Grossauheim; Paul Scherberich, Neu Isenburg; Gerd Schreyer, Grossauheim, all of Germany

[73] Assignee: Deutsche Gold- und Silber-Scheideanstalt vormals Roessler, Frankfurt am Main, Germany

[22] Filed: Nov. 5, 1973

[21] Appl. No.: 413,048

[30] Foreign Application Priority Data
Nov. 9, 1972  Germany............................ 2254701

[52] U.S. Cl............................................. 260/306.7 R
[51] Int. Cl.² ......................................... C07D 277/10
[58] Field of Search .............................. 260/306.7 R

[56] References Cited
UNITED STATES PATENTS

| | | |
|---|---|---|
| 2,879,273 | 3/1959 | Asinger et al................ 260/306.7 R |
| 3,004,981 | 10/1961 | Asinger et al................ 260/306.7 R |
| 3,700,683 | 10/1972 | Asinger et al................ 260/306.7 R |

*Primary Examiner*—Richard J. Gallagher
*Assistant Examiner*—Anne Marie T. Tighe
*Attorney, Agent, or Firm*—Cushman, Darby & Cushman

[57] ABSTRACT

2 and 5 substituted thiazoline-(3) compounds of the formula:

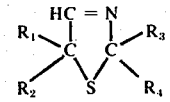

in which $R_1$, $R_2$, and $R_3$ and $R_4$ are the same or different, $R_1$ and $R_2$ are straight or branched chain lower alkyl, alkenyl or aralkyl groups or together are a straight or branched chain alkylene or ethylenically unsaturated divalent aliphatic hydrocarbon group which joins with the adjacent carbon atom to form a ring and $R_3$ and $R_4$ are similarly defined except $R_3$ can also be hydrogen by reaching a 2,2' dioxodisulfide of the formula

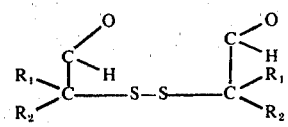

with an oxo compound of the formula

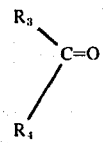

and with ammonia and hydrogen sulfide in the presence of an amine and an ammonium salt.

22 Claims, No Drawings

PROCESS FOR THE PRODUCTION OF THIAZOLINES-(3)

The present invention is directed to a process for the production of 2 and 5 substituted thiazoline-(3) compounds by reacting a 2,2'-dioxodisulfide with an oxo compound, ammonia and hydrogen sulfide.

It is known to produce 2,5,5-substituted thiazoline-(3) compounds by reaction of sulfur with an oxo compound and ammonia in the presence of an amine, see German Offenlegungsschrift No. 1,795,299 and to corresponding Asinger U.S. Pat. No. 3,700,683, the entire disclosure of which is hereby incorporated by reference. According to this process, there can only be obtained 2,5,5-substituted thiazoline-(3) compounds which have a branched chain alkyl group in the 2-position.

It has also been proposed to produce 2,2,5,5-substituted thiazoline-(3) compounds by reaction of 2,2'-dioxodisulfides with oxo compounds, ammonia and hydrogen sulfide, see the Jahrbuch 1967, Landesamt fur Forschung des Landes Nordrhein-Westfalen, pages 21 to 22. This process gives yields of 57% at most.

There has now been found a process for the production in improved yields of 2 and 5 substituted thiazoline-(3) compounds of the formula

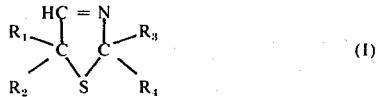

in which $R_1$, $R_2$, $R_3$ and $R_4$ are the same or different, $R_1$ and $R_2$ represent straight or branched chain lower alkyl, alkenyl or aralkyl groups or straight or branched chain lower alkyl or alkenyl groups which form a ring, $R_3$ represents hydrogen and $R_4$ represents straight chain lower alkyl groups or straight or branched chain lower alkenyl or aralkyl groups or $R_3$ and $R_4$ a closed carboxylic ring and $R_3$ and $R_4$ are as defined for $R_1$ and $R_2$ with the further proviso that $R_3$ can be hydrogen. The thiazoline-(3) compounds (I) are prepared by reacting a 2,2'-dioxodisulfide of the formula

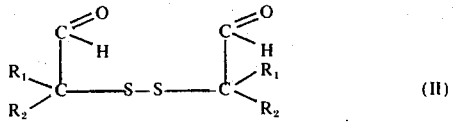

in which $R_1$ and $R_2$ are as defined above with an oxo compound of the formula

where $R_3$ and $R_4$ are as defined above with ammonia and hydrogen sulfide in the presence of an amine and an ammonium salt. There is usually employed an ammonium salt other than ammonium sulfide.

Examples of compounds within the present invention in addition to those set forth in the working examples are 2-methyl-2-propyl-5-ethyl-5-butyl thiazoline-(3); 2,2,5,5-tetraethyl-thiazoline-(3); 2,2-dimethyl-5,5-dihexyl-thiazoline-(3); 2,2-dihexyl-5,5-dimethyl-thiazoline-(3); 2-methyl-2-isopropyl-5,5-dipropyl thiazoline-(3); 2-methyl-2-ethyl-5,5-diisopropyl thiazoline-(3); 2-isopropyl-5,5-dimethyl-thiazoline-(3); 2,2-dimethyl-5,5-dibutyl-thiazoline-(3); 2,2,5-trimethyl-5-amyl thiazoline-(3); 2,5,5-trimethyl-2-hexyl thiazoline-(3); 2,2-dimethyl-5-ethyl,5-sec. butyl thiazoline-(3); 2,2-dimethyl-5-ethyl-5-vinyl thiazoline-(3); 2,2-divinyl-5,5-dimethyl thiazoline-(3); 2-allyl-2,5,5-trimethyl thiazoline-(3); 2-butenyl,2-methyl-5,5-diethyl thiazoline-(3); 2,5-dimethyl,2-ethyl,5-butenyl thiazoline-(3); 2-phenethyl-5,5-dimethyl thiazoline-(3); 2,2-dimethyl-5-benzyl-5-ethyl thiazoline-(3); 2,2,5-trimethyl-5-phenethyl thiazoline-(3); 2,-phenpropyl-2,2,5-trimethyl thiazoline-(3); 2,2,5,5-di(pentamethylene)-thiazoline-(3); 2,2-pentamethylene-5,5 -hexa-methylene thiazoline-(3); 2,2-heptamethylene 5-methyl-5-ethyl thiazoline-(3); 2,2-dimethyl-5,5-octamethylene thiazoline-(3); 2,2-dodecamethylene-5,5-dimethyl thiazoline-(3); 2,2-dimethyl-5,5-undecamethylene thiazoline-(3); 2-methallyl-2-methyl-5-ethyl-5-propyl thiazoline-(3).

The 2,2'-dioxodisulfide of formula II can be prepared for example according to Niederhauser U.S. Pat. No. 2,580,695, the entire disclosure of which is hereby incorporated by reference. There are preferably employed 2,2'-dioxodisulfides in which $R_1$ and $R_2$ are branched or straight chain alkyl groups of 1 to 6 carbon atoms, branched or straight chain alkenyl groups with 2 to 5 carbon atoms or branched or straight chain aralkyl groups having 1 to 3 carbon atoms in the alkyl radical. The alkyl or alkenyl groups can be closed to form rings with the adjacent carbon atom, especially to rings with 5 to 12 carbon atoms. Suitable compounds are for example 2,2'-dithio-bis(2-ethyl butyraldehyde), 2,2'-dithio-bis(2-methyl butyaldehyde), 2,2'-dithio bis (2-phenylpropionaldehyde), 2,2'-dithio-dicyclooctanealdehyde, 2,2'-dithio-dicyclododecanealdehyde, 2,2'-dithio-di-isobutyraldehyde, 2,2'-dithio-di-cyclohexanealdehyde, 2,2'-dithio-di-cyclopentanealdehyde, 2,2'-dithio-di-cyclohexenealdehyde, 2,2'-dithio-di-cyclopentenealdehyde, 2,2'-dithio-bis(2-phenyl butyraldehyde), 2,2'-dithio-bis(2 -phenylvaleraldehyde), 2,2'-dithio-bis(2-benzylbutyraldehyde), 2,2'-dithio bis(2-phenethyl propionaldehyde, 2,2'-dithio bis(2-methylvaleraldehyde), 2,2'-dithio bis(2-methylhexaldehyde, 2,2'-dithio bis(2-methyl octane-aldehyde), 2,2'-dithio bis(2-ethyl isobutyraldehyde), 2,2'-dithio bis(2-methyl sec.valeraldehyde), 2,2'-dithio bis(2-butyl hexaldehyde),2,2'-dithio bis(2-hexyl octaaldehyde), 2,2'-dithio bis(2-methyl crotonaldehyde), 2,2'-dithio bis(2-vinyl propionaldehyde), 2,2'-dithio bis(2-ethyl Δ -4 pentenaldehyde), 2,2'-dithio bis(2-methyl propionaldehyde), 2,2'-dithio bis(2-ethyl hexaldehyde). Preferably compound II is 2,2'-dithio-diisobutyraldehyde or 2,2'-dithio-dicyclohexanaldehyde.

As oxo compound corresponding to formula III there can be especially employed either those in which $R_3$ is hydrogen and $R_4$ is a straight chain or branched alkyl group with 1 to 6 carbon atoms, a straight or branched chain alkenyl group with 2 to 6 carbon atoms or a straight or branched chain aralkyl group with 1 to 3 carbon atoms in the alkyl group or those compounds in which $R_3$ and $R_4$ are straight or branched chain alkyl groups with 1 to 6 carbon atoms, branched or straight chain alkenyl groups with 2 to 6 carbon atoms, branched or straight chain aralkyl groups with 1 to 3 carbon atoms in the alkyl radical. The alkyl or alkenyl groups can be closed to form a ring with the adjacent carbon atom, especially rings with 5 to 12 carbon atoms. Suitable compounds are, for example, acetaldehyde, propionaldehyde, n-butyraldehyde, cyclopentanealdehyde, cyclohexanealdehyde, cyclooctanealdehyde, cyclododecanealdehyde, valeraldehyde, hexanealdehyde, heptanealdehyde, 2-phenylacetaldehyde, 3-phenyl-propionaldehyde, 4-phenylbutyraldehyde, isobutyraldehyde, sec. valeraldehyde, acrolein, crotonaldehyde, Δ-6 hexenaldehyde, acetone, methyl ethyl ketone, diethyl ketone, methyl isobutyl ketone, heptanone-4-phenylacetone, pentanone-2, cyclopentanone, cyclohexanone, dibenzyl ketone, cyclooctanone, cyclododecanone, methyl heptyl ketone, dibutyl ketone, di sec. butyl ketone, diisobutyl ketone, divinyl ketone, diallyl ketone, methyl hexen-1-yl ketone, dimethallyl ketone, methyl vinyl ketone, ethyl vinyl ketone, methyl allyl ketone, methyl butene-1-yl ketone. Especially preferred are acetone, diethyl ketone and cyclohexanone.

The ammonia required for the reaction can be added as such either in aqueous or liquid form or as Diver's solution ($NH_4NO_3 \cdot 2NH_3$). The hydrogen sulfide can be introduced as a gas or can be produced in the reaction mixture by hydrolysis of aliphatic or aromatic thionamides, as for example, thioacetamide.

According to the invention, the reaction of the 2,2'-dioxodisulfide with the oxo compound, the ammonia and the hydrogen sulfide takes place in the presence of an amine. There can be used a single amine or a plurality of amines. While there can be used primary, secondary or tertiary amines, there are preferably used secondary and tertiary amines. There can be used aliphatic amines such as diethyl amine, n-butyl amine, tri-n-butyl amine, tert.butyl amine, sec.butyl amine, ethanolamine, diethanolamine, triethanolamine, cyclohexylamine, trip opanolamine, dipropanolamine, propanolamine, trimethylamine, dimethylamine, propyl butyl amine, dioctylamine, tripropylamine, dipropylamine, propylamine, hexylamine, dihexylamine, trihexylamine, dicyclohexylamine, triethyl amine, laurylamine, allyl amine, cetyl amine, octadecylamine, diisoamylamine, tri n-amylamine, triisoamylamine, heterocyclic amines such as piperazene, morpholine, thiomorpholine, pyridine, piperidine, pyrrolidine, alpha-picoline, beta-picoline, gamma-picoline, butidines, e.g., 2,4-dimethyl pyridine, collidine, pyrrole, N-methyl pyrrole, 2-methyl pyrrole, 2-ethyl pyrrole, pyrimidine, pyrazine, pyrazole, imidazole, aromatic amines such as aniline, o-toluidine, p-toluidine, diphenylamine, N-methyl aniline, N,N-dimethyl aniline, o-aminodiphenyl, alpha-naphthylamine, beta-naphthylamine, 2,3-xylidine, 2,4-xylidine, quinoline, 2-methyl quinoline, p-isopropyl aniline, N-ethyl aniline, N,N-diethyl aniline, 2-aminopyridine. The preferred amines are triethylamine, pyridine, piperidine and triethanolamine.

According to the invention, there is also present an ammonium salt in the reaction. There can be used a single ammonium salt or a mixture of ammonium salts. Salts of both inorganic acids and organic acids are suitable. Thus, there can be used ammonium sulfates, ammonium chloride, ammonium bromide, ammonium hydrogen sulfate, ammonium carbonate, ammonium bicarbonate, ammonium nitrate, monoammonium phosphate, diammonium phosphate, triammonium phosphate, ammonium formate, ammonium acetate, ammonium propionate, ammonium oxalate, ammonium tartrate, ammonium benzoate, ammonium citrate, ammonium oleate, ammonium stearate. The preferred salts are ammonium chloride, ammonium sulfate and ammonium acetate. The ammonium salt can be added as such or can be formed in the reaction mixture from ammonia and the particular acid or acids.

For each mole of 2,2'-dioxodisulfide there are required 2 moles of carbonyl compound III. It is advantageous to employ an excess of carbonyl compound up to about 6 moles (i.e., a total of 8 moles). Preferably there are employed about 4 to 6 moles of carbonyl compound per mole of the 2,2'-dioxodisulfide. There are also required per mole of the 2,2'-dioxodisulfide 2 moles of ammonia and 1 mole of hydrogen sulfide. It is also advantageous to have an excess of these substances, e.g., up to about 4 moles in excess (i.e., a total of 6 moles of ammonium or 5 moles of hydrogen sulfide). Preferably there are used 3 to 4 moles of ammonia and 3 to 4 moles of hydrogen sulfide per mole of 2,2'-dioxodisulfide.

The amines provided in the invention generally should be present in the reaction mixture in an amount of 1 to 5 moles, preferably about 2 to 4 moles per mole of 2,2'-dioxodisulfide. The ammonium salt likewise required by the invention should generally be present in an amount of 0.1 to 4 moles, preferably about 1 to 2 moles per mole of the 2,2'-dioxodisulfide.

While not essential, it can be advantageous to carry out the reaction in an organic solvent. As solvents, there are employed those which are inert to the reactants under the reaction conditions and which are as slightly miscible with water as possible, especially aliphatic hydrocarbons such as benzene fractions, octane, hexane, decane, aromatic hydrocarbons such as benzene, toluene, xylene, p-cymene, cumene, mesitylene, isodurene, tetrahydronaphthalene, ethers such as diethyl ether, dipropyl ether or halogenated hydrocarbons such as chloroform, carbon tetrachloride, 1,1-dichloroethane, 1,2-dichloroethanes, 1,1,1-trichloroethane, 1,1,2-trichloroethane, 1,1,2,2-tetrachloroethane, butyl chloride, amyl chloride, methylene chloride. The solvent, when present, is generally employed in an amount of 200 to 1,000 ml per mole of the 2,2'-dioxodisulfide.

The temperature of reaction is not critical and temperatures between −10°C and the boiling point of the reaction mixture are suitable. It is possible to mix all the materials together in the beginning. However, it can be advantageous to first at least partially react the 2,2'-dioxodisulfide with the hydrogen sulfide in the presence of the amine, and, in a given case, after addition of the inert organic solvent at temperatures between about −10°C and the boiling point of the mixture, especially at temperatures between about 0° and 50°C and then to add the ammonium salt and gradually the carbonyl compound and the ammonia and to carry out the further reaction at temperatures between about 0°C and the boiling point of the mixture, especially at temperatures between about 20° and 80°C.

It can be suitable to drive out the water formed during the reaction. In many cases, it is advantageous to add an entraining agent for this purpose. There can be used for this purpose compounds which form azeotropic mixtures with water but which otherwise behave inertly, for example, benzene, toluene or chloroform. In a given case, there can also serve as the entraining agent the solvent or the carbonyl compound used in excess.

The thiazoline is recovered from the reaction mixture by distillation or preferably by extraction. For the extraction, there are added to the reaction mixture water and, in case the reaction is carried out in the absence of inert organic solvents, such solvents. The pure thiazoline is separated from the solvent phase by distillation or crystallization.

Unless otherwise indicated, all parts and percentages are by weight.

EXAMPLE 1

A mixture of 206 grams (1 mole) of 2,2'-dithio-diisobutyraldehyde, 404 grams (4 moles) of triethylamine and 350 grams (6 moles) of acetone were gassed inside 4 hours at 0° to 10°C with 90 liters (4 moles of hydrogen sulfide). After addition of 107 grams (2 moles) of ammonium chloride and 350 grams (6 moles) of acetone in the course of an hour there were simultaneously introduced into the mixture 10 liters of hydrogen sulfide and 90 liters (4 moles) of ammonia. The temperature was held to 30°C by cooling. After the end of the development of heat there was added 200 ml of water. This mixture was first extracted with 200 ml of diethyl ether and then with 100 ml of diethyl ether. After drying and vaporization of the ether, there were obtained 320 grams of 2,2,5,5-tetramethyl thiazoline(3) having a melting point of 49° to 53°C, corresponding to a yield of 74% based on the 2,2'-dithio-diisobutyraldehyde.

EXAMPLE 2

A mixture of 206 grams (1 mole) of 2,2'-dithio-diisobutyraldehyde, 320 grams (4 moles) of pyridine and 350 grams (6 moles) of acetone, 226 grams (3 moles) of thioacetamide and 60 ml of water were held at 30° to 40°C for 2 hours. After addition of 350 grams (6 moles) of acetone and 230 grams (3 moles) of ammonium acetate the treatment was the same as in Example 1. The yield of 2,2,5,5-tetramethyl thiazoline-(3) amounted to 310 grams corresponding to 72%. The melting point was 50° to 52°C.

EXAMPLE 3

The procedure of Example 1 was carried out. However, there were reacted 206 grams (1 mole) of 2,2'-dithio-di-isobutyraldehyde with 295 grams (3 moles) of cyclohexanone. The yield of 2,2-pentamethylene-5,5-dimethyl thiazoline-(3) was 125 grams, corresponding to 70%. The thiazoline had a boiling point of 52° to 53°C at 1 Torr.

EXAMPLE 4

A mixture of 206 grams (1 mole) of 2,2'-dithio-diisobutyraldehyde, 202 grams (2 moles) of triethylamine and 500 ml of benzene were gassed within 4 hours at 0° to 10°C with 90 liters (4 moles) of hydrogen sulfide. After addition of 344 grams (4 moles) of diethyl ketone and 264 grams (2 moles) of ammonium sulfate in the course of 1 hour there were simultaneously introduced into the mixture 10 liters of hydrogen sulfide and 90 liters (4 moles) of ammonia. Since it was not cooled, the temperature of the mixture held at 75° to 80°C. The water, which formed in the reaction, passed over continuously as an azeotropic mixture with benzene. The further procedure was as in Example 1. There were recovered 120 grams, corresponding to a 76% yield of 2,2-diethyl-5,5-dimethyl thiazoline-(3). It had a boiling point of 50° to 51°C at 1 Torr.

EXAMPLE 5

The procedure of Example 2 was employed but there were reacted 206 grams (1 mole) of 2,2'-dithio-diisobutyraldehyde with 320 grams (3 moles) of benzyl aldehyde. There were recovered 130 grams, corresponding to a 687 yield of 2-benzyl-5,5-dimethyl thiazoline-(3). It had a melting point of 60° to 64°C.

EXAMPLE 6

A mixture of 284 grams (1 mole) of 2,2'-dithio-dicyclohexanealdehyde [dithia-bis-(cyclohexane-1-aldehydyl-(1))], 350 grams (6 moles) of acetone, 505 grams (5 moles) of triethyl amine and 107 grams (2 moles) of ammonium chloride were treated with hydrogen sulfide and ammonia according to the process of Example 1. There were recovered 256 grams of 2,2-dimethyl-5,5-pentamethylene-thiazoline-(3), corresponding to a yield of 70%. The thiazoline had a boiling point of 105° to 108°C at 14 Torr.

EXAMPLE 7

The procedure was the same as in Example 1 but there were reacted 343 grams (1 mole) of dithia-bis-(cyclooctan-1-aldehyde-yl-(1)) with 350 grams (6 moles) of acetone. There were recovered 270 grams of 2,2-dimethyl-5,5-heptamethylene thiazoline-(3) corresponding to a yield of 64%. The thiazoline had a boiling point of 110° to 114°C at 0.5 Torr.

What is claimed is:

1. A process for the production of a thiazoline-(3) compound of the formula

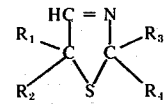

wherein $R_1$ and $R_2$ individually are lower alkyl or ar-lower alkyl groups or $R_1$ and $R_2$ together are an alkylene group which joins with the adjacent carbon atom to form a closed carbocyclic ring, $R_3$ is hydrogen, lower alkyl or ar- lower alkyl, $R_4$ is lower alkyl or ar- lower alkyl or $R_3$ and $R_4$ together are an alkylene group which joins with the adjacent carbon atom to form a closed carbocyclic ring comprising reacting (1) a 2,2'-dioxodisulfide of the formula

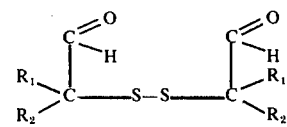

with (2) an oxo compound of the formula

(3) hydrogen sulfide and (4) ammonia in the presence of (5) an amine and (6) an ammonium salt of an acid.

2. A process according to claim 1 wherein $R_1$ and $R_2$ individually are alkyl of 1 to 6 carbons atoms or aralkyl with 1 to 3 carbon atoms in the alkyl group, or $R_1$ and $R_2$ together are alkylene of 5 to 12 carbon atoms, $R_3$ is hydrogen, alkyl of 1 to 6 carbon atoms or aralkyl with 1 to 3 carbon atoms in the alkyl group, $R_4$ is alkyl of 1 to 6 carbon atoms, alkenyl of 2 to 6 carbon atoms or phenylalkyl with 1 to 3 carbon atoms in the alkyl group or $R_3$ and $R_4$ together are alkylene of 5 to 12 carbon atoms.

3. A process according to claim 2 wherein $R_1$ and $R_2$ individually are alkyl of 1 to 6 carbon atoms or benzyl or $R_1$ and $R_2$ together are alkylene of 5 to 12 carbon atoms, $R_3$ is hydrogen, alkyl of 1 to 6 carbon atoms or benzyl, $R_4$ is alkyl of 1 to 6 carbon atoms or benzyl or $R_3$ and $R_4$ together are alkylene of 5 to 12 carbon atoms.

4. A process according to claim 3 wherein $R_1$ is methyl, $R_2$ is methyl or $R_1$ and $R_2$ together are penta methylene or heptamethylene, $R_3$ is hydrogen, methyl or ethyl, $R_4$ is methyl ethyl or benzyl or $R_3$ and $R_4$ together are pentamethylene.

5. A process according to claim 1 wherein the amine is a secondary or tertiary amine.

6. A process according to claim 1 wherein the ammonium salt is an ammonium salt other than ammonium sulfide.

7. A process according to claim 1 wherein there is employed for each mole of dioxodisulfide II from 2 to 8 moles of oxo compound III, from 2 to 6 moles of ammonia, from 1 to 5 moles of hydrogen sulfide, from 1 to 5 moles of amine and from 0.1 to 4 moles of ammonium salt.

8. A process according to claim 2 wherein there is employed for each mole of dioxodisulfide II from 4 to 6 moles of oxo compound III, from 3 to 4 moles of ammonia, from 3 to 4 moles of hydrogen sulfide, from 2 to 4 moles of amine and from 1 to 2 moles of ammonium salt.

9. A process according to claim 8 wherein the amine is a monoalkyl amine, a dialkylamine, a thialkylamine, a monoalkanolamine, a dialkanolamine, a trialkanolamine, a cycloalkylamine, a primary carbocyclic aromatic amine, a secondary carbocyclic aromatic amine, a tertiary carbocyclic aromatic amine or a heterocyclic amine having 5 to 6 carbon atom s in the heterocyclic ring and the ammonium salt is ammonium sulfate, ammonium chloride, ammonium acetate, ammonium bromide, ammonium hydrogen sulfate, ammonium carbonate, ammonium bicarbonate, ammonium nitrate, ammonium phosphate, ammonium salt of a fatty acid having 1 to 18 carbon atoms, ammonium oxalate, ammonium tartrate, ammonium citrate or ammonium benzoate.

10. A process according to claim 7 carried out in the presence of an inert organic solvent.

11. A process according to claim 7 carried out at $-10°C$, to the boiling point of the mixture.

12. A process according to claim 7 wherein the hydrogen sulfide is added as such.

13. A process according to claim 12 wherein the hydrogen sulfide is added as a compound which decomposes to form hydrogen sulfide in situ.

14. A process according to claim 13 wherein the decomposable compound is thioacetamide.

15. A process according to claim 7 wherein the dioxodisulfide II is in a first step reacted with at least a part of the hydrogen sulfide in the presence of the amine and thereafter in a second step there is added the ammonia, the ammonia salt and the oxo compound III.

16. A process according to claim 7 wherein the dioxodisulfide II is 2,2'-dithio-di-isobutyraldehyde or 2,2'-dithio-di-cyclohexanealdehyde, the oxo compound III is acetone, diethyl ketone or cyclohexanone.

17. A process according to claim 16 wherein the amine is triethylamine, pyridine, piperidine or triethanolamine and the ammonium salt is ammonium chloride, ammonium sulfate or ammonium acetate.

18. A process according to claim 16 wherein the oxo compound is acetone.

19. A process according to claim 3 wherein the amine is a secondary or tertiary amine.

20. A process according to claim 3 wherein the ammonium salt is an ammonium salt other than ammonium sulfide.

21. A process according to claim 1 wherein the ammonium salt is an ammonium salt other than ammonium sulfide.

22. A process according to claim 1 wherein $R_1$ and $R_2$ individually are lower alkyl or aralkyl with 1 to 3 carbon atoms in the alkyl group or $R_1$ and $R_2$ together are alkylene of 5 to 12 carbon atoms, $R_3$ individually is hydrogen, lower alkyl or aralkyl with 1 to 3 carbon atoms in the alkyl group or $R_3$ and $R_4$ together are alkylene of 5 to 12 carbon atoms.

* * * * *